US008512769B2

(12) United States Patent
Feistel et al.

(10) Patent No.: US 8,512,769 B2
(45) Date of Patent: Aug. 20, 2013

(54) VALERIAN EXTRACT PREPARATION

(75) Inventors: Björn Feistel, Andernach (DE); Hartwig Sievers, Neustadt (DE); Romanus Lehnfeld, Herzogenaurach (DE)

(73) Assignee: Finzelberg GmbH & Co. KG, Andernach (DE)

( * ) Notice: Subject to any disclaimer, the term of this patent is extended or adjusted under 35 U.S.C. 154(b) by 185 days.

(21) Appl. No.: 12/311,381

(22) PCT Filed: Sep. 25, 2007

(86) PCT No.: PCT/EP2007/060153
§ 371 (c)(1),
(2), (4) Date: Dec. 22, 2009

(87) PCT Pub. No.: WO2008/037707
PCT Pub. Date: Apr. 3, 2008

(65) Prior Publication Data
US 2010/0119630 A1    May 13, 2010

(30) Foreign Application Priority Data
Sep. 27, 2006 (DE) .......................... 10 2006 045 974

(51) Int. Cl.
*A61K 36/00* (2006.01)
*A61K 36/84* (2006.01)

(52) U.S. Cl.
USPC ......................................... 424/733; 424/725

(58) Field of Classification Search
None
See application file for complete search history.

(56) References Cited

U.S. PATENT DOCUMENTS 3,485,851 A * 12/1969 Thies ........................... 549/332
2006/0138052 A1 * 6/2006 Leistner et al. ............... 210/692

FOREIGN PATENT DOCUMENTS

| CN | 1 129 567 A | 8/1996 |
|----|----|----|
| CN | 1 191 137 A | 8/1998 |
| EP | 0 363 777 A1 | 10/1989 |
| GB | 2351978 A | 1/2001 |
| WO | WO 02092113 A1 * | 11/2002 |

OTHER PUBLICATIONS

Marder et al, 6-methylapigenin and hesperidin: new *Valeriana* flavonoids with activity on the CNS, Pharmacology, biochemistry, and behavior, (Jun. 2003) vol. 75, No. 3, pp. 537-545.*

Hattesohl, et al., "Effects of extracts from *Valeriana officinalis* L. in pharmacological studies," Planta Medica, vol. 72, No. 11, Sep. 2006, p. 1064, abstract only.

Matsunaga et al., "Effects of Chinese and Paraguayan Medicinal Plants on the Duration of Immobility of Mice in the Forced Swimming Test," Natual Medicines, vol. 51, No. 1, 1997, pp. 63-66.

Sakamoto et al., "Psychotropic Effects of Japanese *Valerian* Root Extract," Chemical and Pharmaceutical Bulletin, vol. 40, No. 3, 1992, pp. 758-761.

Izquierdo et al., "The effect of *Valerian* (*Valerian officinalis* L.) in growth inhibition and its anxiolytic activity in mice," Revista Mexicana de Ciencias Farmaceuticas, vol. 32, No. 4, 2001, pp. 24-28.

Hattesohl, et al., "Extracts of *Valeriana officinalis* L. s.l. show anxiolytic and antidepressant effect but neither sedative nor myorelaxant properties," Phytomedicine, vol. 15, No. 1-2, Jan. 2008, pp. 2-15.

Wasowski et al., "Isolation and Identification of 6-Methylapigenin, a Competitive Ligand for the Brain GABAA Receptors, from *Valeriana wallichii*," Planta Med , 68:934-936 (2002).

* cited by examiner

*Primary Examiner* — Qiuwen Mi
(74) *Attorney, Agent, or Firm* — Dardi & Herbert, PLLC; Peter S. Dardi (57) ABSTRACT

Process for preparing a valerian extract formulation comprising the steps of:

a) extracting radix valeriana officinalis with alcoholic-aqueous extractants to obtain a raw extract, said alcoholic-aqueous extractant containing from 10 to 50% by volume of alcohol;

b) at least partially removing the alcoholic fraction from the raw extract to obtain a viscous extract;

c) contacting the viscous extract with a hydrophobic adsorbing agent;

d) separating the hydrophobic adsorbing agent to obtain a purified extract;

e) converting the purified extract to a valerian extract formulation using pharmaceutically acceptable auxiliary agents.

11 Claims, 4 Drawing Sheets

Fig.1a

\* = significant compared to control with p < 0.05
\*\* = significant compared to control with p < 0.01
\*\*\* = significant compared to control with p < 0.001

* = significant compared to control with p < 0.05
** = significant compared to control with p < 0.01
*** = significant compared to control with p < 0.001

Fig.4

VALERIAN EXTRACT PREPARATION

RELATED APPLICATION

This application is a national stage filing of PCT Application No. PCT/EP2007/060153 filed Sep. 25, 2007, which claims priority to German Patent Application No. 102006045974.1 filed Sep. 27, 2006, each of which are hereby incorporated herein by reference.

TECHNICAL FIELD OF THE INVENTION

The present invention relates to a novel valerian extract formulation, a process for the preparation thereof, and the use thereof.

Valerian root (radix valeriana officinalis) has long been employed in conditions of unrest as well as anxiety-produced sleep-onset insomnia. Despite numerous examinations, it has not been completely clarified which components are responsible for the activity.

INTRODUCTION TO THE INVENTION

WO 98/13054 describes that valepotriates have sedative properties. However, since valepotriates are virtually insoluble in aqueous and aqueous-alcoholic solvents, they are practically not detectable in aqueous or alcoholic extracts of radix valeriana.

Other components to which the activity is in part attributed include valerenic acids, sesquiterpene compounds. Typical valerian extracts are standardized for their content of valerenic acids.

WO 98/13054 describes extracts obtained by $CO_2$ extraction, thus having high contents of both valerenic acid and valepotriates.

U.S. Pat. No. 6,383,526 describes a process for preparing a valerian extract in which the extraction is effected with 50 to 100% (v/v) ethanol (typically 70%). This reduces the content of valepotriates to obtain extracts having high contents of valerenic acids. An anxiolytic effect has been described for such extracts.

It is the object of the present invention to provide valerian extract formulations having improved properties, especially an enhanced anxiolytic or antidepressive effect.

DESCRIPTION OF THE INVENTION

Surprisingly, it has been found that this object can be achieved by a process for preparing a valerian extract formulation comprising the steps of:
a) extracting radix valeriana with alcoholic-aqueous extractants to obtain a raw extract, said alcoholic-aqueous extractant containing from 10 to 50% by volume of alcohol;
b) at least partially removing the alcoholic fraction from the raw extract to obtain a viscous extract;
c) contacting the viscous extract with a hydrophobic adsorbing agent;
d) separating the hydrophobic adsorbing agent to obtain a purified extract;
e) converting the purified extract to a valerian extract formulation using pharmaceutically acceptable auxiliary agents.

Thus, in the process according to the invention, radix valeriana officinalis is first extracted with an alcoholic-aqueous extractant. Typically, the dried plant is comminuted (8-12 mm) to facilitate extraction. A suitable weight ratio between the dried plant and extractant is within a range of about from 1:5 to 1:30, preferably from 1.10 to 1:20.

The skilled person knows that the extraction can be improved by heating the extractant. Suitable temperatures for extraction are from room temperature to about 70° C., preferably in a range of from 40 to 60° C.

The longer the extraction lasts, the more components can be extracted. On the other hand, extract components may also be damaged by the temperature treatment during extraction. Typical extraction times are from 1 to 12 hours, preferably from 2 to 6 hours.

In contrast to the processes described in the prior art, the extraction is performed with an extractant containing a rather low proportion of alcohol. The content of alcohol is from 10 to 50% by volume of the extractant, preferably from 20 to 45% by volume, more preferably from 30 to 40% by volume. Suitable alcohols include, in particular, ethanol, but also methanol, isopropanol and mixtures thereof.

After the extraction, the extractant is separated from the dry plant residue. Suitable methods for this purpose are filtration, suction, draining etc.

Subsequently, the alcoholic fraction of the thus obtained raw extract is completely or partially removed. This can be done, for example, by means of a bubble evaporator or a plate evaporator. By adding more water, the proportion of alcohol can be reduced, for example, <2% by weight. The resulting proportion of dry substance is from 40 to 70% (m/m).

The thus obtained aqueous extract is referred to as "viscous extract" in the following.

In the next step, the viscous extract is contacted with a hydrophobic adsorbing agent. It is desirable for the adsorber to have a high surface area (>200 $m^2/g$) in order to be able to adsorb a large amount of substance. Resins having uniform pore sizes (100 to 450 Å) are found to be particularly advantageous. Artificial resin adsorbers have proven particularly suitable, for example, those based on divinylbenzene copolymers, aliphatic ester polymers or formophenol polymers. Preferably, the adsorbers employed have no functional groups like quaternary ammonium compounds or acid functions, as are usual with ion-exchangers. Particularly suitable substances are obtainable under the trade name Amberlite®. Suitable products include XAD4, XAD2, XAD16, XAD761, XAD1180, XAD160, XAD7HP. Analogous characterized adsorber resins, e.g., from the company Diaion, from the company Bayer (Lewatit®) or from the company Miontech, may also be used.

Said contacting of the viscous extract with a hydrophobic adsorbing agent can be performed with methods familiar to the skilled person, for example, by filling the adsorber material into a column through which the viscous extract is subsequently flowed (optionally after being diluted). An alternative thereof is a batch process in which the adsorbing agent is added and separated again after a dwelling time.

After the hydrophobic adsorbing agent has been separated, a valerian extract is obtained that can be further treated in a way known to the skilled person. Preferably, the extract is dried. This can be effected, for example, by lyophilization, spray drying, vacuum drying etc. During spray drying and vacuum drying, auxiliary agents are preferably added in order to obtain a free-flowing dry extract.

The invention also relates to a valerian extract formulation obtainable by the process according to the invention.

Surprisingly, the valerian extract formulation according to the invention exhibits a relatively low content of total valerenic acids ($\leq 0.18$% by weight) and a relatively low content of valepotriates ($\leq 0.1$% by weight), respectively based on the dry extract.

Typically, the contents of total valerenic acids are distributed as follows:

<0.10% by weight valerenic acid;
<0.1, more preferably <0.07, even more preferably <0.05% by weight, acetoxyvalerenic acid;
≦0.01, preferably <0.01% by weight, hydroxyvalerenic acid;
respectively based on the dry extract.

Unless stated otherwise, all percentages are by weight.

Figure 3:
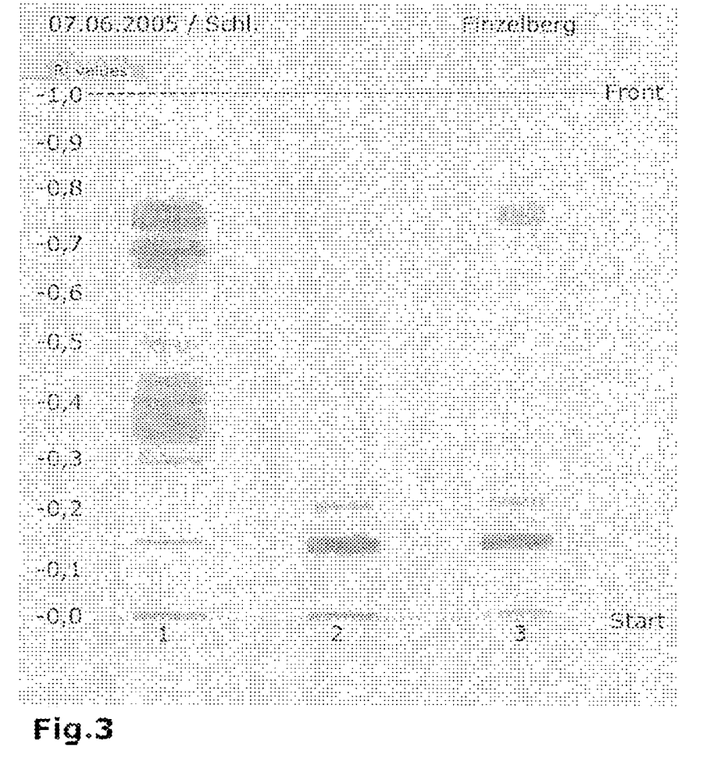
FIG. 3 shows a thin-layer chromatographical analysis of the fractions obtained.
Figure 4:
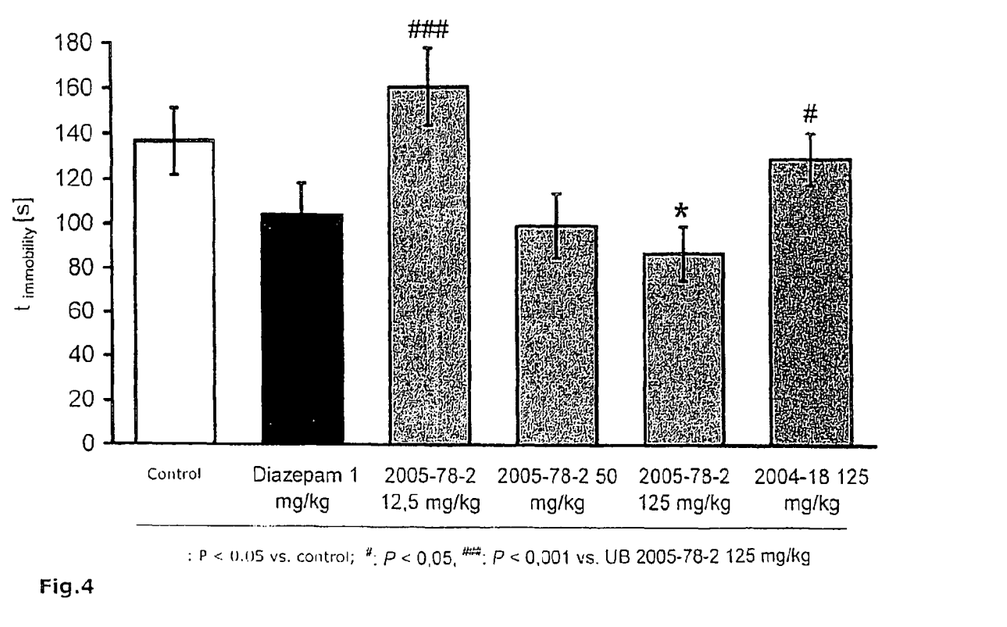
FIG. 4 shows a forced swimming test using the extract according to the invention as compared to a non-purified extract after twice daily peroral administration for 16 days.

The process causes a depletion of particularly lipophilic components, characterized by an absence or a highly reduced concentration in the $R_f$ range of from 0.3 to 0.8 as compared to the starting extract (see FIG. 3). The thin-layer chromatographic conditions (according to FIG. 3) are as follows:

| | |
|---|---|
| stationary phase (TLC plate material): | silica gel 60 $F_{254}$ |
| mobile phase (solvent): | see mobile solvent |
| mobile solvent | dichloroethane:acetic acid:methanol:water 50:25:15:10 (v/v/v/v) (with about 30 min equilibration of the plate and TLC chamber with mobile solvent) |
| separating distance | 15 cm (start to front) |
| running time | about 2 hours |
| drying | about 10 min in a flow of cold air |
| spray reagent | anisaldehyde reagent 0.5 ml of anisaldehyde is mixed with 10 ml of anhydrous acetic acid, 85 ml of methanol and 5 ml of 96% sulfuric acid in the stated order |
| drying | about 3 min at 120° C. until the color development of the zones has reached its optimum |
| sample solution | 1 g of valerian extract is dissolved with 10 ml of 50% ethanol v/v for 10 min in a water bath at 65° C. After cooling to room temperature, the mixture is filtered to clarity, and the clear filtrate is used for chromatography. 10 µl is applied by an application device. |

The extract formulation according to the invention preferably has a herb-to-extract ratio of from 3:1 to 10:1, preferably from 4:1 to 6:1.

The invention also relates to a medicament containing the valerian extract formulation according to the invention, and the use of the valerian extract formulation according to the invention for preparing a medicament for inhibiting or releasing anxiety (anxiolytic) and for reducing depressions or depressive moods (antidepressive).

The critical point is that the anxiolytic property and antidepressive property are not achieved by a sedating activity, but no sedative effect is observed, as shown in Examples 7 and 8.

The extract obtained can be simply converted to a pharmaceutical formulation, for example, in the form of tablets, capsules, lozenges.

In particular, dosages of about 100 to 1000 mg per unit dose have proven suitable, wherein preferably about 1 to 3 dose units are to be taken per day.

EXAMPLES

The invention is illustrated further by the following Examples.

Example 1

Preparation of the Viscous Extract 10 kg of radix valerianae officinalis (valerenic acids 0.18%) was admixed with 35% v/v ethanol at a ratio of 1:16 and percolated to exhaustion at 50° C. in a Holstein & Kappert extractor. The eluate was drained from the dry plant and freed from dry plant residues through a 250 µm bubble bag passage. The percolate was concentrated in a plate evaporator and turned solvent-free by adding water. 4.6 kg of viscous extract having a dry matter content of 60.3% resulted as the yield.

Example 2a

Purification by Hydrophobic Absorber XAD-4

From the product, a fraction of 663.3 g of viscous extract, corresponding to 400 g of dry extract equivalent, was diluted with demineralized water to 10% dry matter content and homogenized with stirring for 30 minutes. A dark homogeneous solution resulted.

It was applied to a hydrophobic adsorber resin (Amberlite XAD-4) in a glass column filled with about 4 l of moist resin, corresponding to about 1600 g of dry resin. The purification step was performed at a rate of 3 bed volumes of resin per hour.

After the purification of the starting extract solution, it could be found that 85% of the initial amount was still present. This solution was evaporated and then converted to a dry extract formulation with the drying auxiliary maltodextrin at a ratio of 70% native:30% maltodextrin per spray drying run (UB 2005-37-2).

Example 2b

Purification by Hydrophobic Absorber XAD-1180

Based on a valerian viscous extract according to Example 1, a fraction of 2.7 kg of extract, corresponding to 1628 g of dry extract equivalent, was diluted with demineralized water to 10% dry matter content, and homogenized with stirring for 30 minutes. A dark homogeneous solution resulted.

It was applied to a hydrophobic adsorber resin (XAD-1180) in a column filled with about 20 l of moist resin, corresponding to about 8000 g of dry resin. The purification step was performed at a rate of 3 bed volumes of resin per hour. After the purification of the starting extract solution, it could be found that 81% of the initial amount was still present.

This solution was evaporated into a viscous extract and then converted to a dry extract formulation with the drying auxiliary maltodextrin at a ratio of 70% native:30% maltodextrin per spray drying run (UB 2005-78-2). This valerian extract formulation had a drying loss of 4.6% and contained <0.02% valepotriates, 0.112% total valerenic acids, among which 0.06% valerenic acid, 0.04% acetoxyvalerenic acid and 0.002% hydroxyvalerenic acid.

Example 3

Residue on the Adsorber

The substances retained on the adsorber in Example 2a were eluted by elution with 2 bed volumes of ethanol 96% v/v. This solution was also evaporated into a viscous extract and then converted to a dry extract formulation with the drying auxiliary maltodextrin at a ratio of 70% native:30% maltodextrin per spray drying run (UB 2005-37-1).

Example 4

Content of Valerenic Acids

Subsequently, the valerenic acids of the extracts according to Examples 2a) and 3 were determined.

|  | lipophilic ethanol phase of adsorber inclusion (Example 3) | purified water phase after adsorber contact (Example 2a)) |
|---|---|---|
| Total valerenic acids in dry extract | 0.73% | 0.13% |

Example 5

Comparative Example without Purification

Based on the valerian viscous extract according to Example 1, a dry extract formulation was prepared with the drying auxiliary maltodextrin at a ratio of 70% native:30% maltodextrin per spray drying run (UB 2004-18). This valerian extract formulation had a drying loss of 3.0% and contained 0.04% valepotriates, 0.29% total valerenic acids, among which 0.12% valerenic acid, 0.14% acetoxyvalerenic acid and 0.03% hydroxyvalerenic acid.

Example 6

Anxiolytic Activity

The Elevated Plus Maze (EPM) is a widely employed and acknowledged behavioral model useful for examining the anxiety behavior of rats or mice and enabling the detection of substances having an anxiolytic or anxiogenic effect. It is based on the observation that unconditioned rats or mice respond with spontaneous avoidance behavior to natural aversive stimuli.

Based on studies by Montgomery, Pellow introduced the EPM for the first time in 1985 (Pellow, S., et al., 1985. Validation of open:closed arm entries in an elevated plus-maze as a measure of anxiety in the rat, J. Neurosci. Methods 14, 149-167).

The EPM is a plus-shaped experimental device placed in an elevated position with a square central platform where two closed and two open arms are respectively opposing each other. The closed arms have a high border whereas the open arms may be enclosed by a narrow bar. The closed arms represent a protected area that allows the test animal to take cover whereas the open arms have an aversive effect.

Animals allowed to freely explore all the areas of the maze over a defined period of time will avoid the open arms and prefer the closed areas, which is expressed by a shorter dwelling time on the open arms and a reduced number of entries into the latter. The avoidance behavior caused by anxiety overweighs the curiosity to explore a new environment ("exploratory behavior").

During a test period, the number of entries into the open and closed arms and the time spent on the open and closed arms are recorded. Both parameters are increased by substances having an anxiolytic effect and reduced by anxiogenic ones.

False positive results can be produced only by motility-enhancing substances; they are eliminated by evaluating the respective percentages rather than absolute values (Hogg, S., 1996. A review of the validity and variability of the elevated plus-maze as an animal model of anxiety, Pharmacol. Biochem. Behav. 54, 21-30).

The EPM allows a reliable detection of benzodiazepines (e.g., Diazepam®). Since a wide variety of factors (light, acoustic stimuli) influence the model, a validation of the test system must be performed first.

Each tested substance is to be compared with a reference substance. With appropriate handling and evaluation, anxiolytic and anxiogenic effects are reliably indicated. After such precautions, false positive results are almost excluded.

The tests of the valerian formulations in the EPM were performed with female NMRI mice (n=10-14) using the following experimental set-up:

| Animal strain | Sex | Text history | Food | Bars (open arms) | Color of arm surface |
|---|---|---|---|---|---|
| NMRI | female | naive | not deprived | no bars | black |

Reference Extracts

The following results were found for different extracts obtained from one dry plant lot:

| Extractant | Water | Comparative extract EtOH 35% v/v | Comparative extract EtOH 70% v/v | Supercritical carbon dioxide |
|---|---|---|---|---|
| Herb-to-extract ratio native | 3.3:1 | 3.1:1 | 4.0:1 | 40:1 |
| Content of total valerenic acids | 0.05% | 0.25% | 0.80% | 12.70% |
| Content of valepotriates | <0.02% | <0.02% | <0.02% | 11.6% |

-continued

| Extractant | Water | Comparative extract EtOH 35% v/v | Comparative extract EtOH 70% v/v | Supercritical carbon dioxide |
|---|---|---|---|---|
| Anxiolytic properties in EPM model (female NMRI mice fasted, n = 10, 60 min after oral administration), 250 mg/kg of body weight | | | | |
| Percentage of dwelling time on open arms | +10% | +24% | +17% | +11% |
| Percentage of entries into open arms | +6% | +18% | +8% | −3% |
| Rating | not significant | significant compared to control group | not significant | not significant |

Extracts According to the Invention

Extract according to the invention, lot #UB 2007-37-2 according to Example 2a)

| Extractant | EtOH 35% v/v |
|---|---|
| Purification | passage through adsorber column with XAD-4 resin |
| Herb-to-extract ratio native | 4.2:1 |
| Content of total valerenic acids | 0.13% |
| Content of valepotriates | <0.01% |
| Anxiolytic properties in EPM model (female NMRI mice fasted, n = 10, 60 min after oral administration), 250 mg/kg of body weight | |
| Percentage of dwelling time on open arms | +16% |
| Percentage of entries into open arms | +17% |
| Rating | highly significant compared to control group |

Figure 1A:
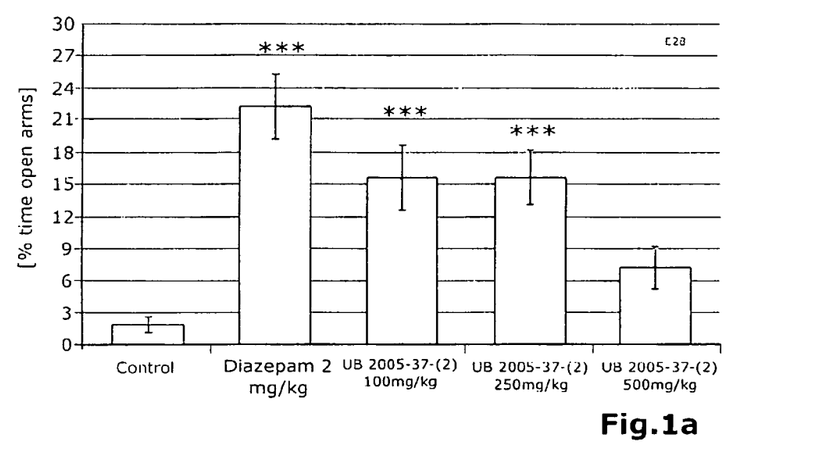
FIG. 1a/b shows an EPM test after administration of the valerian extract purified according to the invention.
Figure 1B:
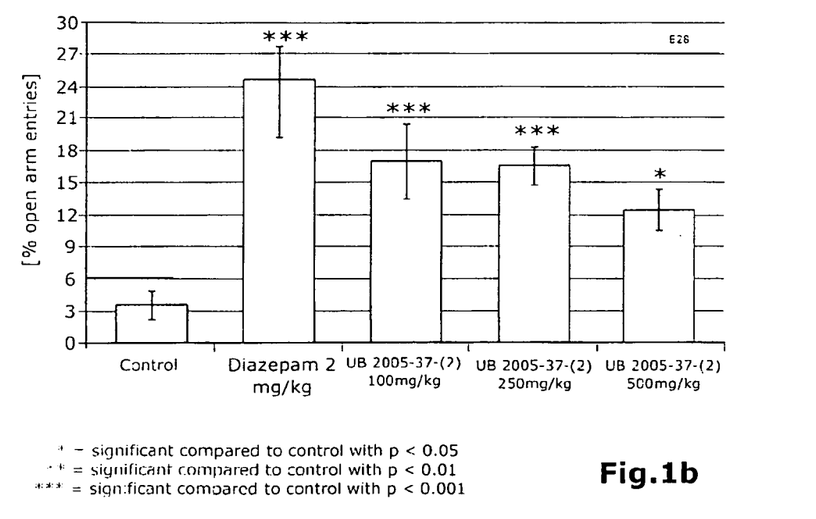

FIGS. 1a/b show the EPM test after administration of the valerian extract purified according to the invention as obtained in Example 2a).

FIG. 1a) shows the time spent on open arms.

FIG. 1b) shows the number of entries into open arms.

As compared to the control, a clear anxiolytic effectiveness is shown at 100 and 200 mg/kg of body weight. The effect of an optimum dose range, typical of plant extracts, is also shown, since a higher dosage does not exhibit an improved effectiveness.

Residual Fractions

Separated residual fraction from extract according to the invention, lot #UB 2007-37-1 according to Example 3

| Extractant | EtOH 35% v/v |
|---|---|
| Purification | ethanolic eluate from adsorber column with XAD-4 resin |
| Herb-to-extract ratio native | 4.2:1 |
| Content of total valerenic acids | 0.73% |
| Content of valepotriates | 0.21% |
| Anxiolytic properties in EPM model (female NMRI mice fasted, n = 10, 60 min after oral administration), 250 mg/kg of body weight | |
| Percentage of dwelling time on open arms | +12% |
| Percentage of entries into open arms | +11% |
| Rating | lower values compared to control group, indifferent to contrary effect (anxiogenic) |

Figure 2A:
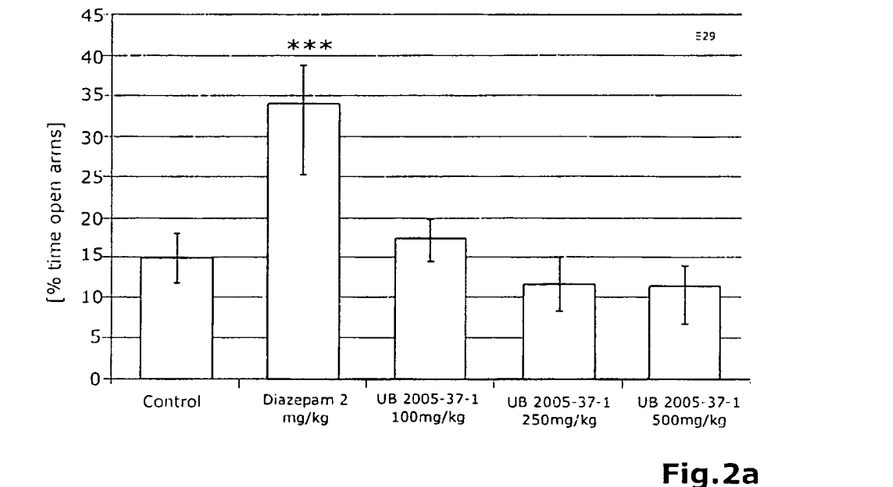
FIG. 2a/b shows an EPM test using the residual fraction from the purification.
Figure 2B:
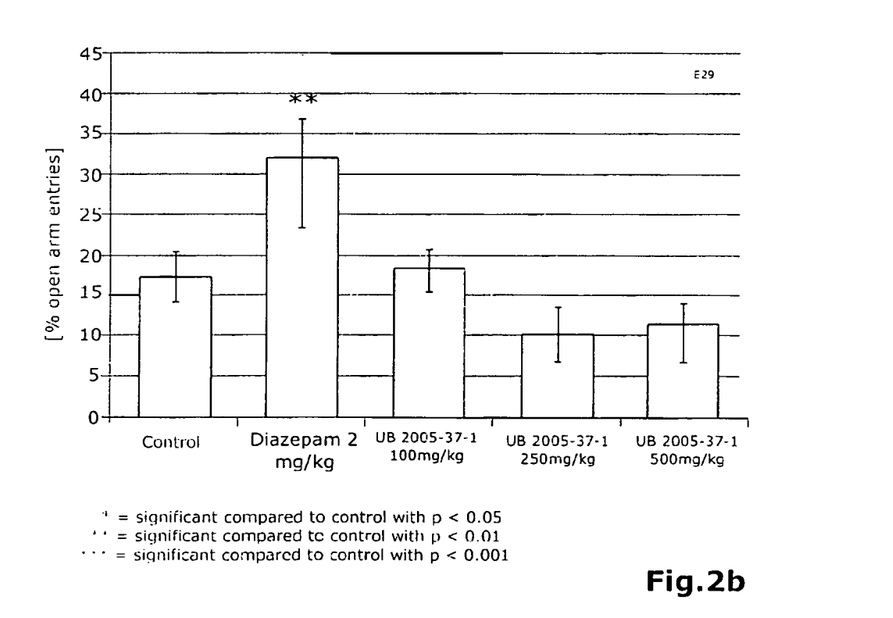

The residual fraction from the adsorber (Example 3) was additionally examined. FIGS. 2a/b show the examination of this substance in the EPM.

FIG. 2a) shows the dwelling time on open arms.

FIG. 2b) shows the number of entries into open arms.

It is shown that the substance found in the adsorber having a high content of valerenic acids even has a rather anxiogenic effect. By the process according to the invention, substances having an antagonistic effect on anxiolysis are selectively depleted.

FIG. 3 shows the thin-layer chromatographical analysis of the fractions.

Lane 3: raw extract obtained according to Example 1.

Lane 2: extract according to the invention according to Example 2a).

Lane 1: residual fraction elutable from the adsorber according to Example 3.

Example 7

Test for Sedative Effect

The sedative effect was tested by examining the spontaneous motility. For this purpose, NMRI mice (Charles River, Sulzfeld, Germany, n=8 per group) were tested for a sedating effect by means of infrared technology immediately after administration of the testing solution by measuring the motor activity. Thus, line trespasses are measured within a 10 minute period in a cage. As compared to the control, the extract according to the invention had no sedative effect.

Example 8

Test for Duration of Anesthesia

In another test, the ether-induced duration of anesthesia was examined in female NMRI mice (Charles River, Sulzfeld, Germany, n=8). A prolongation of anesthesia could not be observed; this also shows that the extract formulations according to the invention have no sedative effect.

Example 9

Examination of Antidepressive Effect

A more specific test for antidepressive activity is provided by the forced swimming test (FST) developed by Porsolt (Porsolt et al., 1978. Behavioural despair in rats: a new model sensitive to antidepressant treatments, Eur. J. Pharmacol. 47, 379-391).

In a so-called "forced swimming test", the test animals (rats) are challenged by a stress situation from which they cannot escape by their own efforts. For this purpose, rats are at first left in a water-filled glass cylinder for a time of 15 minutes in a preliminary test (conditioning) one day before the actual test. The filling level is matched to the animals' body weight, so that every animal can support itself with the paws and tail and can keep its nose above water with minimum swimming movements. After an extended phase of vigorous swimming and diving movements, the animals learn that escape from the situation is not possible and adopt a characteristic, almost motionless, hunched posture with almost closed eyelids ("despair behavior"). Twenty-four hours after this preliminary test, the test with valerian extract is performed in which the rats are again inserted into the water cylinders and the duration of immobility over a period of 5 minutes is cumulatively recorded.

For testing the valerian formulations on male CD rats, a pretreatment was used for 16 days, and the formulation according to Example 2b) was employed. Five hours after the last treatment, the rats were inserted into transparent acrylic glass cylinders having a diameter of 18 cm and a height of 40 cm. Prior to each experimental run, the cylinders were filled with water of 25° C.±1° C., the filling level being 17-20 cm depending on the rat's weight. The experiment was recorded by means of a video camera, and the time of immobility of the animals was later detected manually on the screen.

Antidepressives such as Diazepam cause a shortening of the immobility time, and the animals remain in the active swimming phase for a longer time.

In this test, 1 mg/kg Diazepam shortened the immobility time by 28% as compared to the control group. For a primary extract from valerian roots with 35% EtOH (UB 2004-18, Example 5), no change as compared to the control group was found at a dosage of 125 mg/kg. In contrast, the valerian extract according to the invention after purification over hydrophobic adsorbers (UB 2005-78-2, Example 2b)) reached a reduction of immobility time by 36%, which was statistically significant compared to the control group, at the same dosage of 125 mg/kg.

Further, a statistically highly significant difference between a concentration of 12.5 mg and the ten times higher dosage of 125 mg is found.

Example 10

Preparation of Viscous Extract 10.5 kg of radix valerianae officinalis (valerenic acids 0.23%) was filled into an extractor and treated with hot steam from bottom to top for 3 hours. Volatile components were removed from the extractor and condensed. The aqueous condensate within and outside the extractor was discarded. Subsequently, the thus pretreated dry plant was admixed with 30% v/v ethanol at a ratio of 1:14 and percolated to exhaustion at 40° C. in a Holstein & Kappert extractor. The eluate was drained from the dry plant and freed from dry plant residues through a 250 μm bubble bag passage. The percolate was concentrated in a plate evaporator and turned solvent-free by adding water.

4.9 kg of viscous extract having a dry matter content of 66.0% resulted as the yield. Based on the native dry extract, <0.02% valepotriates, 0.015% iso-valeric acid, 0.23% total valerenic acids, among which 0.11% valerenic acid, 0.09% acetoxyvalerenic acid and 0.03% hydroxy-valerenic acid, are contained.

Example 11

Extract According to the Invention

A fraction of 606 g of extract of Example 10, corresponding to 400 g of dry extract equivalent, was diluted with demineralized water to 10% dry matter content, and homogenized with stirring for 30 minutes. A dark homogeneous solution resulted.

It was applied to a hydrophobic adsorber resin (XAD-4) in a glass column filled with about 4 l of moist resin, corresponding to about 1600 g of dry resin. The purification step was performed at a rate of 3 bed volumes of resin per hour. After the purification of the starting extract solution, it could be found that 83% of the initial amount was still present.

This solution was evaporated into a viscous extract and then converted to a dry extract formulation with the drying auxiliary maltodextrin at a ratio of 80% native:20% maltodextrin per spray drying run (UB 2006-66).

This low-odor valerian extract formulation had a drying loss of 4.0% and contained <0.02% valepotriates, 0.008% isovaleric acid, 0.113% total valerenic acids, among which 0.07% valerenic acid, 0.04% acetoxyvalerenic acid and 0.003% hydroxyvalerenic acid.

Testing in an EPM model for anxiolytic properties gave the following results for a 100 mg dose per kg of body weight of female NMRI rats 60 in after oral administration: prolongation of the time spent on open arms by 30%; increase of the number of entries into open arms by 25%, as compared to the control.

Example 12

Preparation of a Pharmaceutical Composition

The extract according to the invention is subjected to direct tabletting with the following formulation:
300 mg of valerian dry extract according to the invention
160 mg of microcrystalline cellulose
25 mg of sodium carboxymethylcellulose
10 mg of highly disperse silica
5 mg of magnesium stearate The resulting tablet is coated with a layer of Eudragit E100 for reducing the typical valerian smell.
Results of the Experiments The extract according to the invention combines both antidepressive and anxiolytic activity without exhibiting a generally sedative effect.

The invention claimed is:

1. A process for preparing a valerian extract formulation comprising the steps of:
   a) extracting radix valeriana officinalis with alcoholic-aqueous extractants to obtain a raw extract, said alcoholic-aqueous extractant containing from 10 to 50% by volume of alcohol;
   b) at least partially removing the alcoholic fraction from the raw extract to obtain a viscous extract;
   c) contacting the viscous extract with a hydrophobic adsorbing agent;
   d) separating the hydrophobic adsorbing agent to obtain a purified extract;
   e) converting the purified extract to a valerian extract formulation using pharmaceutically acceptable auxiliary agents wherein the valerian extract formulation does not exhibit a generally sedative effect.

2. The process according to claim 1, wherein said alcohol is selected from methanol, ethanol, isopropanol and mixtures thereof.

3. The process according to claim 1, wherein said alcohol in the raw extract is removed by evaporation.

4. The process according to claim 1, wherein said hydrophobic adsorber is selected from the group consisting of divinylbenzene copolymers, aliphatic ester polymers and formophenol polymers.

5. The process according to claim 1, wherein said valerian extract formulation is converted to a dry extract formulation together with drying auxiliaries.

6. A valerian extract formulation obtainable by a process according to claim 1.

7. The valerian extract formulation according to claim 6, having a content of at most:
   total valerenic acids ≦0.18% by weight, among which
      acetoxyvalerenic acids <0.1%;
      hydroxyvalerenic acids <0.01%;
   valepotriates ≦0.1% by weight, respectively based on the native dry extract.

8. The valerian extract formulation according to claim 6, characterized in that its herb-to-extract ratio is from 3:1 to 10:1.

9. A medicament or food supplement containing a valerian extract formulation according to claim 6.

10. A method for inhibiting or releasing anxiety in a living subject comprising administering a medicament or food supplement comprising an effective amount of the valerian extract formulation of claim 6.

11. A method for reducing depressions or depressive moods in a living subject comprising administering a medicament or food supplement comprising an effective amount of the valerian extract formulation of claim 6.

* * * * *